(12) United States Patent
Koo et al.

(10) Patent No.: US 7,998,902 B2
(45) Date of Patent: Aug. 16, 2011

(54) USE OF 5-BENZYLOXYMETHYL-1,2-ISOXAZOLINE DERIVATIVES AS A HERBICIDE

(75) Inventors: Suk-Jin Koo, Daejeon (KR); Ki-Hwan Hwang, Daejeon (KR)

(73) Assignee: Moghu Research Center Ltd., Eoeun-Dong, Yuseong-Gu, Daejeon (KR)

( * ) Notice: Subject to any disclaimer, the term of this patent is extended or adjusted under 35 U.S.C. 154(b) by 0 days.

(21) Appl. No.: 12/122,312

(22) Filed: May 16, 2008

(65) Prior Publication Data
US 2008/0318784 A1 Dec. 25, 2008

(30) Foreign Application Priority Data
Jun. 22, 2007 (KR) .......................... 10-2007-0061711

(51) Int. Cl.
*A01N 43/74* (2006.01)
*A01N 43/80* (2006.01)
(52) U.S. Cl. ....................................... 504/271; 504/100
(58) Field of Classification Search .................. 504/100, 504/271
See application file for complete search history.

(56) References Cited

U.S. PATENT DOCUMENTS
4,060,402 A * 11/1977 Tomita et al. ................. 504/179
4,983,210 A    1/1991 Rheinheimer et al.
6,838,416 B2 *  1/2005 Ryu et al. ...................... 504/271

FOREIGN PATENT DOCUMENTS
JP    A 9-143171      6/1997
KR    10-0392072 B1   7/2003

* cited by examiner

*Primary Examiner* — Fereydoun Sajjadi
*Assistant Examiner* — Danielle Sullivan
(74) *Attorney, Agent, or Firm* — Robert E. Bushnell, Esq.

(57) ABSTRACT

The present invention relates to a turf herbicide comprising, as an active ingredient, of 5-benzyloxymethyl-1,2-isoxazoline derivatives of formula (I), which have been known as an a rice paddy herbicide. In addition, 5-benzyloxymethyl-1,2-isoxazoline derivatives of the present invention have a high activity not only as a turf herbicide but also as a herbicide for upland crops and direct-seeded rice. As such, the derivatives of the present invention can be used either as an upland herbicide or as a herbicide for direct-seeded paddy field rice.

10 Claims, 4 Drawing Sheets

//USE OF
5-BENZYLOXYMETHYL-1,2-ISOXAZOLINE
DERIVATIVES AS A HERBICIDE

DETAILED DESCRIPTION OF THE INVENTION

Purpose of the Invention

Figure 1:
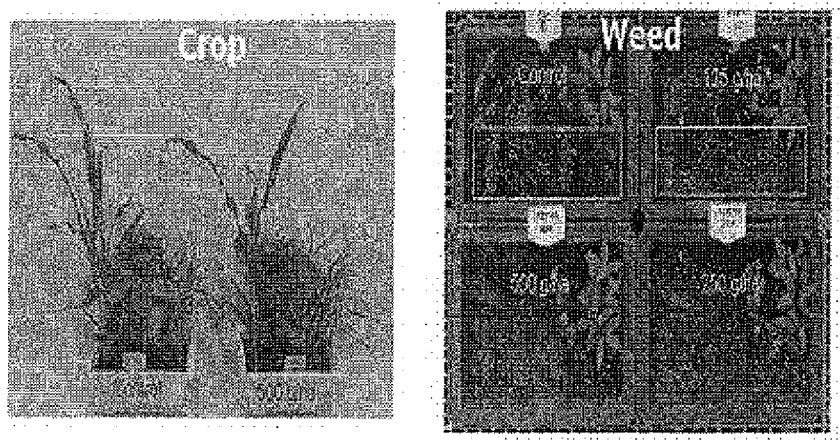
FIG. 1 shows the herbicidal activity of the test substance of the present invention when it was applied as pre-emergence treatment in an upland condition. The photo on the left is for the crops; specifically, from the left side of the pot, there are corn (ZEAMX), soybean (GLYMX), cotton (GOSHI), wheat (TRIAZ) and rice (ORYSA). The left pot is the control group to which the test substance was not applied and the right pot is the one after application with the test substance at a dosage of 500 g/ha. The photo on the right is for the weeds; specifically, the upper left pot is the control group without any treatment, and others are after application with the test substance at a dosage of 125, 250, or 500 g/ha, clockwise starting from the control. Inside each pot, broadleaf weeds such as common cocklebur (XANST), Indian joint-vetch (AESIN), velvetleaf (ABUTH), morningglory (IPOSP) were planted in the top part of the pot while in the bottom part the gramineous weeds such as barnyardgrass (ECHCG), large crabgrass (DIGSA), green foxtail (SETVI), fall panicum (PANDI) were planted. As seen from the photo, the test substance showed a remarkable effect of controlling all of the gramineous weeds at a dosage of 125 g/ha or more, while it had almost no effect to the broadleaf weeds.
Figure 2:
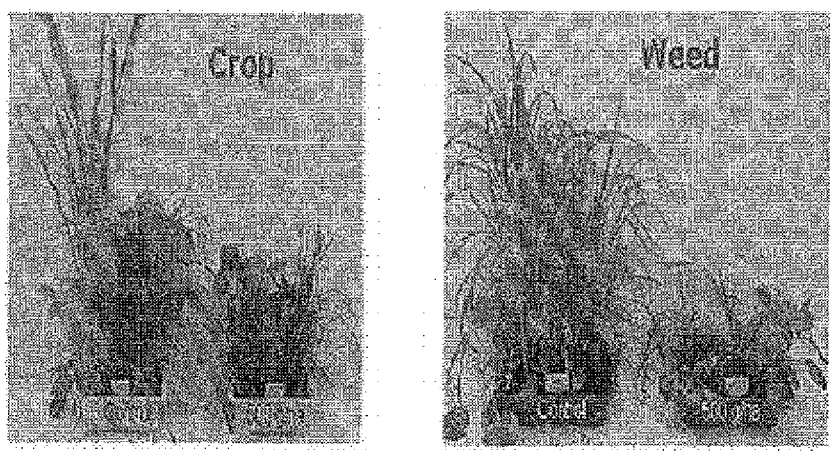
FIG. 2 shows the herbicidal activity of the test substance of the present invention when it was applied as post-emergence treatment in an upland condition. Especially, the test substance was applied to the crops and the weeds after they have already grown to a certain growth stage (i.e., three-leaf stage). The photo on the left is for the crops wherein the left pot is a control group while the right pot is for the treatment with the test substance at a dosage of 500 g/ha. The photo on the right is for the weeds, indicating that the gramineous weeds were well controlled while the broad-leaf weeds were somewhat controlled showing a mild suppression effect.

Technical Field of the Invention and Prior Art

The present invention relates to uses of 5-benzyloxymethyl-1,2-isoxazoline derivatives, which had been reported as a paddy rice herbicide, as a herbicide for upland, turf, and direct-seeded rice.

Korean Patent Registration No. 392072 discloses a rice paddy herbicide which comprises as an active ingredient 5-benzyloxymethyl-1,2-isoxazoline derivative compounds represented by following formula (I):

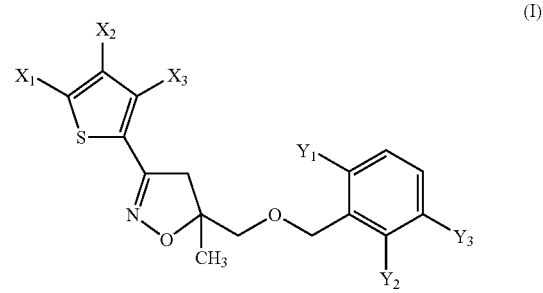

wherein, $X_1$, $X_2$ and $X_3$ are each a hydrogen, a methyl group, a halogen group, a methoxy group or a nitro group (provided that all of $X_1$, $X_2$ and $X_3$ cannot be a hydrogen at the same time); and $Y_1$, $Y_2$ and $Y_3$ are each a hydrogen or a fluorine.

It has been already indicated in U.S. Pat. No. 4,983,210 and Japanese Patent No. 09,143,171 that the above-described 5-benzyloxymethyl-1,2-isoxazoline derivative compound as a paddy field herbicide is better than the isoxazoline derivatives of prior art in terms of safety of rice crops and when applied to soil it has herbicidal activity of controlling various types of weeds that are found in a rice paddy field such as barnyardgrass, *Scirpus juncoides* Roxb., *Monochoria vaginalis* Presl., *Cyperus serotinus* Rottb., and *Sagittaria pigmaea* Miq., etc.

However, other than as a herbicide for rice paddy field, there has been no other uses described in said documents for 5-benzyloxymethyl-1,2-isoxazoline derivative compound represented by the above-stated general formula (I).

There are two main types of herbicide being used, i.e., one for paddy field and the other for upland field. Depending on the place it is applied, the method and rate of a herbicide may vary.

The inventors of the present invention found that 5-benzyloxymethyl-1,2-isoxazoline derivative compounds, which had been reported to be a good herbicide for transplanted paddy rice, also had an excellent crop safety for upland crops, turfgrasses, and direct-seeded rice and controlled various important grass weeds; therefore, the said compound(s) are excellent selective herbicide(s) for upland crops, turfgrasses, and direct-seeded rice. As a result, the present invention has been completed.

Technical Subject to be Achieved by the Present Invention

Object of the present invention is to provide an upland herbicide, turf herbicide, or a herbicide for direct-seeded rice which comprises as an active ingredient 5-benzyloxymethyl-1,2-isoxazoline derivative compound represented by the above-described general formula (I).

The other object of the present invention is to provide 5-(2,6-difluorobenzyl)oxymethyl-5-methyl-3-(4-methylthiophen-5-yl)-1,2-isoxazoline compound which has an excellent activity as a field herbicide, a turf herbicide or a herbicide for direct-seeded rice.

CONSTITUTION OF THE INVENTION

In order to achieve the above-stated object, the present invention provides 5-benzyloxymethyl-1,2-isoxazoline derivative compounds represented by the following general formula (I) as an upland herbicide, a turf herbicide or a herbicide for direct-seeded paddy field rice:

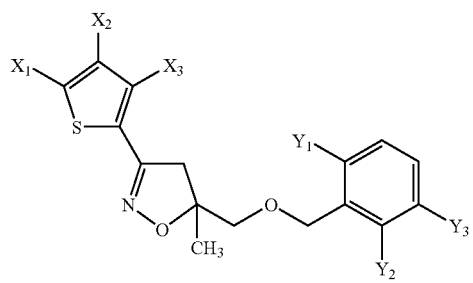

(I)

wherein, $X_1$, $X_2$ and $X_3$ are each a hydrogen, a methyl group, a halogen group, a methoxy group or a nitro group (provided that all of $X_1$, $X_2$ and $X_3$ cannot be a hydrogen at the same time); and $Y_1$, $Y_2$ and $Y_3$ are each a hydrogen or a fluorine.

Furthermore, the present invention provides 5-(2,6-difluorobenzyl)oxymethyl-5-methyl-3-(4-methylthiophen-5-yl)-1,2-isoxazoline compound (herein after referred to as "test substance") represented by the following formula (II), which is included in the above general formula (I) and has an activity as a field herbicide, a turf herbicide or a herbicide for direct-seeded paddy field rice:

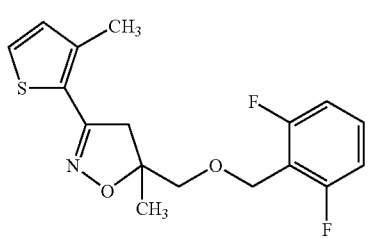

(II)

Furthermore, the present invention provides a field herbicide, a turf herbicide or a herbicide for direct-seeded paddy field rice which comprises the compound of general formula (I) or formula (II) as an active ingredient and a solid carrier, a liquid carrier or a surfactant. The solid carriers which can be comprised in the herbicide of the present invention includes the following: inorganic powder such as kaolin, bentonite, montmorilonite, talc, diatomite, mica, gypsum, calcium carbonate, apatite and silicon hydroxide; plant powder such as soybean flour, wheat flour, saw dust, tobacco powder, starch powder and crystalline cellulose; polymeric material such as petroleum resin, vinyl chloride resin and ketone resin; alumina; and wax. The liquid carriers which can be comprised in the herbicide of the present invention includes the following: alcohols such as methanol, ethanol, ethylene glycol and benzyl alcohol; aromatic hydrocarbons such as benzene, toluene, xylene and methyl naphthalene; halogenated hydrocarbons such as chloroform, carbon tetrachloride and chlorobenzene; ethers such as dioxane and tetrahydrofuran; ketones such as acetone, methylethyl ketone and cyclohexanone; esters such as ethyl acetate, butyl acetate and ethylene glycol acetate; amides such as dimethylformamide; nitrites such as acetonitrile; ether alcohols such as ethyl glycol and ethyl ether; and water. The surfactants which can be comprised in the herbicide of the present invention includes the following: cationic surfactants such as bromocetyltrimethyl ammonium salt; anionic surfactants such as alkyl aryl sulfonic acid, alkyloxy sulfonic acid, aryl sulfonic acid, alkaline metal salts, alkaline earth metal salts and ammonium salts thereof; and non-ionic surfactants such as aliphatic alcohols, castor oil, a condensate between naphthalene or naphthalene sulfonate and phenol or formaldehyde.

In a single active ingredient formulation as an upland herbicide, a turf herbicide or a herbicide for direct-seeded rice, the compound of general formula (I) or formula (II) is comprised in an amount of 1 to 80% by weight (w/w) based on the total weight of the final product. In addition, as an active ingredient in a mixture with one or more other active ingredients, it is preferably comprised in an amount of 1 to 40% by weight (w/w) based on the total weight of the final product.

The present invention further provides 5-(2,6-difluorobenzyl)oxymethyl-5-methyl-3-(4-methylthiophen-5-yl)-1,2-isoxazoline compound represented by the formula (II), which has an excellent herbicidal activity against the gramineous weeds when it is applied to a field, a turf or a direct-seeded paddy field rice.

The gramineous weed is one of the most common weeds found in crop field and non-agricultural lot. When the compound of 5-(2,6-difluorobenzyl)oxymethyl-5-methyl-3-(4-methylthiophen-5-yl)-1,2-isoxazoline was applied to several major crops including corn, soybean, wheat and cotton, etc. before or after germination, the gramineous weeds were selectively controlled. Furthermore, when warm season turfgrass such as Zoysiagrass or cool season turfgrass such as bentgrass, Kentucky bluegrass, perennial rye grass, etc. were applied with said compound before or after the germination, it was confirmed that various types of gramineous weeds including large crabgrass and annual bluegrass were selectively controlled. Still furthermore, for direct-seeded rice plant, it was also confirmed that various types of gramineous weeds including barnyardgrass, Chinese sprangletop (*Lep-* tochloa chinensis), saramollagrass (*Ischaemum rugosum*), and *Isachne globosa* and other weeds were also selectively controlled by pre-emergence or post-emergence treatment. Thus, 5-benzyloxymethyl-1,2-isoxazoline derivative compound of the present invention can be used as an upland herbicide, a turf herbicide or a herbicide for direct-seeded rice.

The present invention further provides a method for selective control of barnyardgrass, green foxtail, fall panicum, or large crabgrass in corn, soybean, wheat, cotton, hot pepper, Chinese cabbage, sesame, onion, garlic, tomato or potato before or after the germination with 5-benzyloxymethyl-1,2-isoxazoline derivative compound of the above-described general formula (I) or 5-(2,6-difluorobenzyl)oxymethyl-5-methyl-3-(4-methylthiophen-5-yl)-1,2-isoxazoline of the above-described formula (II).

The present invention further provides a method for selective control of large crabgrass or annual bluegrass in warm season (zoyisagrass) and cool season turf including bentgrass, Kentucky bluegrass, perennial ryegrass before or after the germination by applying with 5-benzyloxymethyl-1,2-isoxazoline derivative compound of the above-described general formula. (I) or 5-(2,6-difluorobenzyl)oxymethyl-5-methyl-3-(4-methylthiophen-5-yl)-1,2-isoxazoline of the above-described formula (II).

The present invention still further provides a method for selective control of barnyardgrass, Chinese sprangletop (*Leptochloa chinensis*), saramollagrass (*Ischaemum rugosum*), and *Isachne globosa* by pre-emergence or post-emergence treatment to direct-seeded rice plant by applying with 5-benzyloxymethyl-1,2-isoxazoline derivative compound of the above -described general formula (I) or 5-(2,6-difluorobenzyl)oxymethyl-5-methyl-3-(4-methylthiophen-5-yl)-1,2-isoxazoline of the above-described formula (II).

Herein below, the present invention is described in greater detail with reference to the following examples. However, they are only to exemplify the present invention and in no case it is construed that the present invention is limited thereto.

EXAMPLES

Example 1

Evaluation of Field Herbicidal Activity of 5-(2,6-difluorobenzyl)oxymethyl-5-methyl-3-(4-methylthiophen-5-yl)-1,2-isoxazoline (Herein After Referred to as "Test Substance")

The test substance used in the present invention was provided from Korean Research Institute of Chemical Technology (KRICT), the owner of Korean Patent Registration No. 0392072.

To a rectangular plastic pot having a surface area of 300 $cm^2$, mixed soils comprising blend bed soil (Boonong, Horticultural Bed Soil No. 3) and sandy loam soil were filled (mixing ratio, 1:1). Seeds of the eight different types of weeds including gramineous weed such as barnyardgrass, large crabgrass, green foxtail, fall panicum, and broadleaf weed such as common cocklebur, velvetleaf, Indian joint-vetch, and morningglory were sown. To the other pot containing the same soil mixture, seeds of the five different types of crops including corn, soybean, cotton, wheat and rice were sown. Pots were kept in a greenhouse of which temperature was maintained at 25~30° C. (day) or 15~25° C. (night), and regularly watered.

After fourteen days and when the crops and the weeds reached their three-leaf stage, the other set of a crop pot and a weed pot were prepared by the same method as described above. Then, "test substance" was sprayed thereto. In this case, spray treatment to the plants after they have grown for two weeks corresponded to post-emergence treatment while spray treatment to the seeds right after the sowing corresponded to pre-emergence treatment. Spray was carried out by using a track sprayer (R&D Sprayer, USA) equipped with a Teejet 8002 nozzle (Spraying Systems Co., USA). Spray volume was adjusted to 300 L/ha. The spray solution was prepared by dissolving the "test substance" in acetone and adding the same volume of 0.2% (v/v) Tween 20 aqueous solution. Dosage of the test substance was 500, 250, 125, 62.5 or 31.3 g/ha. Two weeks after the spray of the test substance, efficacy and phytotoxic effect to the crops and the weeds were visually measured based on a 0 to 10 scale (0: no efficacy, 10: completely killed). The results are summarized in the following Table 1.

TABLE 1

The activity of the test substance measured in an upland condition (pot test).

| Dosage (g/ha) | Crops | | | | | Gramineous weed | | | | Broad-leaf weed | | | |
|---|---|---|---|---|---|---|---|---|---|---|---|---|---|
| | Corn | Rice | Wheat | Soybean | Cotton | Barnyard grass | Foxtail | Fall panicum | Barnyard grass | Cocklebur | Velvetleaf | Indian joint-vetch | Morning glory |
| Pre-emergence treatment: Soil treatment ||||||||||||||
| 500 | 0 | 0 | 0 | 0 | 0 | 10 | 10 | 10 | 10 | 0 | 0 | 0 | 2 |
| 250 | 0 | 0 | 0 | 0 | 0 | 10 | 9 | 9 | 10 | 0 | 0 | 0 | 2 |
| 125 | 0 | 0 | 0 | 0 | 0 | 10 | 9 | 9 | 9 | 0 | 0 | 0 | 1 |
| 62.5 | 0 | 0 | 0 | 0 | 0 | 4 | 3 | 8 | 9 | 0 | 0 | 0 | 0 |
| 31.2 | 0 | 0 | 0 | 0 | 0 | 2 | 1 | 5 | 1 | 0 | 0 | 0 | 0 |
| Post-emergence treatment: Foliar spray at three leaf stage of the weeds ||||||||||||||
| 500 | 8 | 0 | 0 | 6 | 0 | 9 | 9 | 8 | 9 | 7 | 6 | 4 | 3 |
| 250 | 3 | 0 | 0 | 2 | 0 | 7 | 5 | 6 | 6 | 3 | 3 | 3 | 1 |
| 125 | 2 | 0 | 0 | 0 | 0 | 3 | 2 | 3 | 5 | 1 | 1 | 2 | 0 |
| 62.5 | 2 | 0 | 0 | 0 | 0 | 2 | 1 | 1 | 3 | 0 | 0 | 1 | 0 |
| 31.2 | 0 | 0 | 0 | 0 | 0 | 0 | 0 | 0 | 1 | 0 | 0 | 0 | 0 |

*Visual measurement: 0, no efficacy/no phytotoxic effect; 10, completely killed

Figure 3:
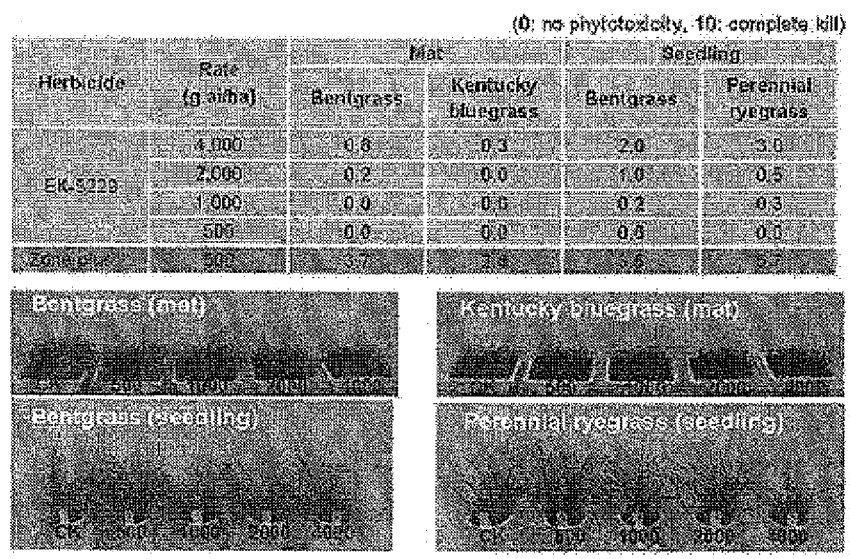
FIG. 3 shows a safety test result of the test substance of the present invention to turf species. Specifically, the photo on the left is bentgrass and one on the right is cool season turfgrass including Kentucky bluegrass and perennial ryegrass. "Mat" indicates that a transplanted commercial sod used for an experiment while "Seedling" indicates that the turf grass was grown by direct seeding. In each photo, the one at the far left side corresponds to a control group while the remaining indicates the treatment with the test substance at a dosage described therein. There was no phytotoxicity for bentgrass both in "Mat" and "Seedling" group at a dosage as high as 4,000 g/ha. It was also safe to Kentucky bluegrass and perennial ryegrass.

As shown in the above Table 1, when the test substance of the present invention was applied at pre-emergence timing to the crops such as corn, rice, wheat, soybean and cotton, it was completely safe without any phytotoxic effect to the crops at dosage of 500 g/ha. On the other hand, the gramineous weeds such as barnyardgrass, green foxtail, large crabgrass and fall panicum were effectively controlled at dosage of 125 g/ha or more. Broadleaf weeds were not affected (see, FIG. 1). In the case of post-emergence treatment, the test substance was not safe to corn and soybean (i.e., strong phytotoxic effect was observed). However, it was safe to rice, wheat and cotton. It was found that at the dosage of 500 g/ha most of the gramineous weeds were controlled while the herbicidal effect decreased at lower application rate (FIG. 3). In post-emergence application, broadleaf weeds in addition to grassy weeds are well controlled at 500 g/ha. According to these results, it was found that the test substance of the present invention had a higher safety and better herbicidal efficacy in pre-emergence treatment than in post-emergence treatment. In pre-emergence application, and its weed control spectrum corresponded to gramineous weeds.

Based on the above results, it is confined that the compound of the present invention can be used, by pre and post-emergence application, for controlling gramineous weeds in upland crops such as corn, wheat, soybean and cotton, etc. besides paddy rice. In addition, because there is no herbicidal effect to broadleaved plants by the test substance of the present invention, it its believed that the compound of the present invention can be used for selective control of gramineous weeds in fruits and vegetables such as hot pepper, Chinese cabbage, sesame, onion, garlic, tomato and potato that belong to broad-leaf plant family.

Example 2

Use as a Turf Herbicide

From the results of the above Example 1, it was confirmed that the test substance of the present invention has an excellent effect of controlling gramineous weeds such as large crabgrass. Meanwhile, large crabgrass is one of the major target weeds to be controlled not only for crops but also for turf (e.g., golf course and amenity area, etc.). As such, once safety is proven for turfgrass, the compound can be used as a turf herbicide. Thus, the test substance of the present invention was tested to evaluate safety to several kinds of warm and cool season turfgrasses.

Commercially available sod mats of zoysiagrass and bentgrass, Kentucky bluegrass, and perennial ryegrass were purchased. After cutting each turf sod mat in a size of 10 cm×20 cm, it was transplanted to a rectangular plastic pot having a surface area of 300 $cm^2$ wherein mixed soils comprising blend of a bed soil (Boonong, Horticultural Nursery Soil No. 3) and sandy loam soil were filled (mixing ratio, 1:1). After transplanting, the grass was mowed (0.5~1.0 cm in height) once a week, and kept for one month in a greenhouse maintained at 25~30° C. (day) or 15~25° C. (night), then the test substance of the present invention was applied at dosage of 4, 2, 1 and 0.5 kg/ha. As a reference, Dithiopyr (32% EC, manufactured by Dongbu Hannong Chemical Company, KOREA) was applied at the recommended rate of 0.48 kg/ha, or twice or quadruple amount thereof, i.e., 0.96 and 1.92 kg/ha, respectively. Spray was made by a track sprayer equipped with a Teejet 8002 nozzle. Spray volume was adjusted to 2,000 L/ha, which was a typical value for an Asian (Korea and Japan) golf course. The spray solution was prepared by dissolving the "test substance" in acetone and adding the same volume of 0.2% (v/v) Tween 20 aqueous solution. Two, four or six weeks after the spray of the test substance, phytotoxicity to the turfgrass were visually evaluated based on 0 to 10 scale (0: no phytotoxic effect, 10: completely killed). The test was conducted in a randomized block design with a three replicates and the results were summarized in the following Table 2 is an average value of the replicates.

TABLE 2

Safety test (i.e., phytotoxic effect measurement) for the test substance and the control herbicide*

| | | Warm season turf grass | | | Cold season turf grass | | | | | | | | |
|---|---|---|---|---|---|---|---|---|---|---|---|---|---|
| | Dosage | Zoysiagrass | | | Bentgrass | | | Kentucky bluegrass | | | Perennial ryegrass | | |
| Substance | (kg/ha) | Week 2 | Week 4 | Week 6 | Week 2 | Week 4 | Week 6 | Week 2 | Week 4 | Week 6 | Week 2 | Week 4 | Week 6 |
| Test substance | 4 | 2.7 | 1.7 | 1.0 | 2.3 | 3.0 | 2.0 | 2.8 | 3.0 | 1.0 | 3.0 | 2.7 | 2.0 |
| | 2 | 1.3 | 0.2 | 0.0 | 2.3 | 1.7 | 1.0 | 2.7 | 1.3 | 0.0 | 2.7 | 1.3 | 1.0 |
| | 1 | 0.7 | 0.0 | 0.0 | 1.8 | 0.5 | 0.2 | 0.8 | 0.7 | 0.0 | 0.7 | 0.3 | 0.0 |
| | 0.5 | 0.0 | 0.0 | 0.0 | 1.3 | 0.2 | 0.0 | 0.3 | 0.2 | 0.0 | 0.3 | 0.0 | 0.0 |
| | 0.25 | 0.0 | 0.0 | 0.0 | 0.8 | 0.0 | 0.0 | 0.0 | 0.0 | 0.0 | 0.0 | 0.0 | 0.0 |
| Dithiopyr | 1.92 | 3.7 | 3.3 | 3.0 | 3.3 | 4.2 | 4.2 | 3.7 | 4.2 | 4.2 | 3.3 | 2.7 | 2.3 |
| | 0.96 | 2.3 | 1.5 | 1.3 | 2.3 | 1.7 | 2.0 | 2.2 | 2.7 | 2.7 | 2.0 | 2.0 | 1.3 |
| | 0.48 | 1.0 | 1.0 | 0.7 | 1.5 | 0.3 | 0.3 | 1.5 | 0.5 | 0.7 | 1.3 | 0.3 | 0.3 |

*Visual assessment: 0, no phytotoxic effect; 10, completely killed

Figure 4:
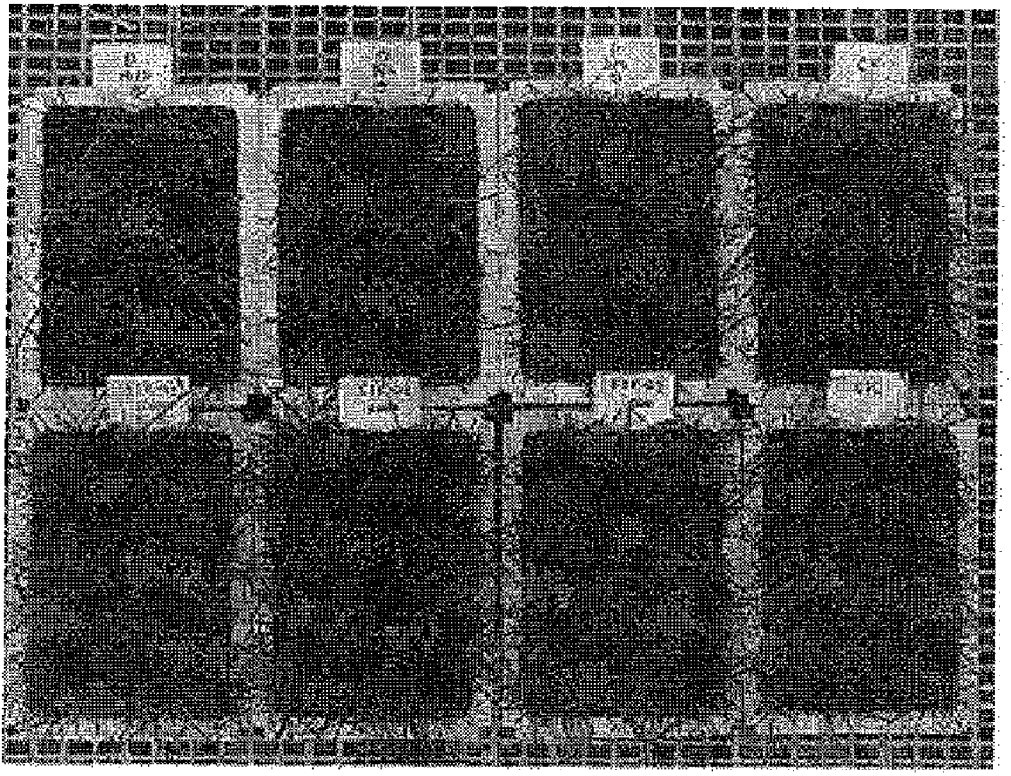
FIG. 4 shows a result of comparative experiment between the test substance of the present invention and a commercial herbicide, Dithiopyr, tested for Kentucky bluegrass. Pots in the top panel correspond to the Dithiopyr-treated group [1,920 (4×standard rate), 960 (2×standard rate), 480 (standard rate) g ai/ha] and the control group while the bottom panel corresponds to the test substance-treated group [4000 g, 2000 g, 1000 g ai/ha] and the untreated control group, respectively. Dithiopyr somewhat suppressed the growth of turfgrass even at a standard rate, and phytotoxicity was more evident for two or four times of the standard rate (i.e., 2× and 4×). On the other hand, the test substance showed no phytotoxicity at all at a dosage as high as 4,000 g/ha.
Figure 5:
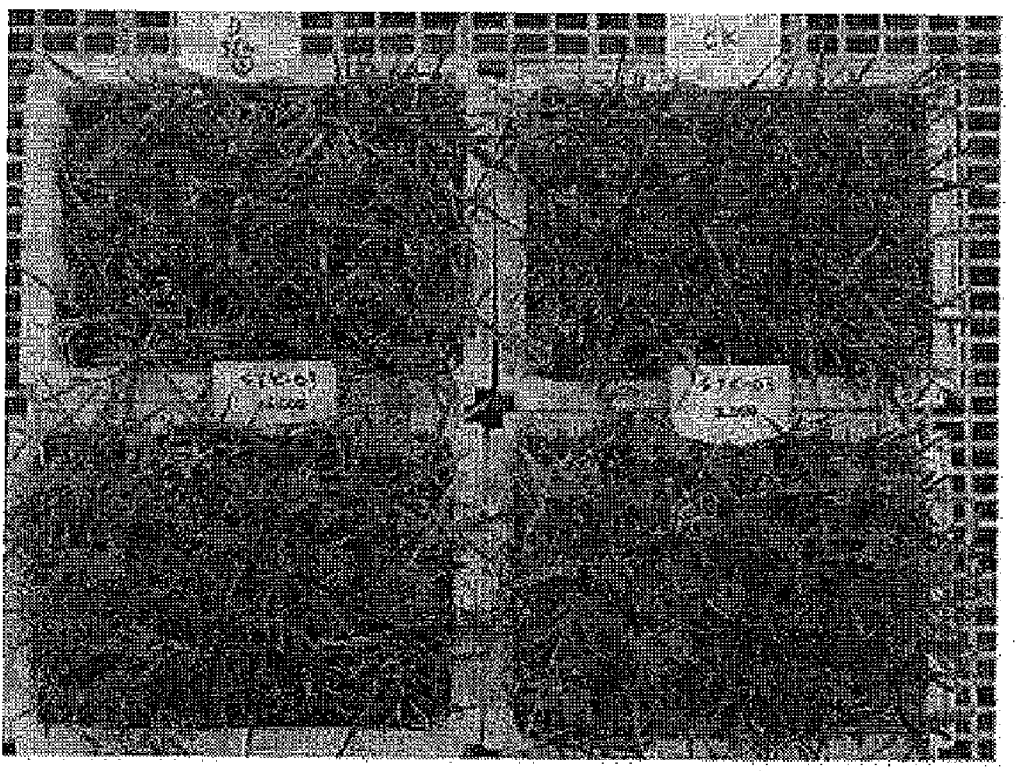
FIG. 5 shows phytotoxicity tested against zoysiagrass (*Zoysia japonica*). The photo on the left shows Dithiopyr treated zoyisagrass clearly evidencing the phytotoxicity. However, in the bottom panel wherein the test substance of the present invention was treated in a rate of 4,000 or 2,000 g/ha, no phytotoxicity was observed at all.
Figure 6:
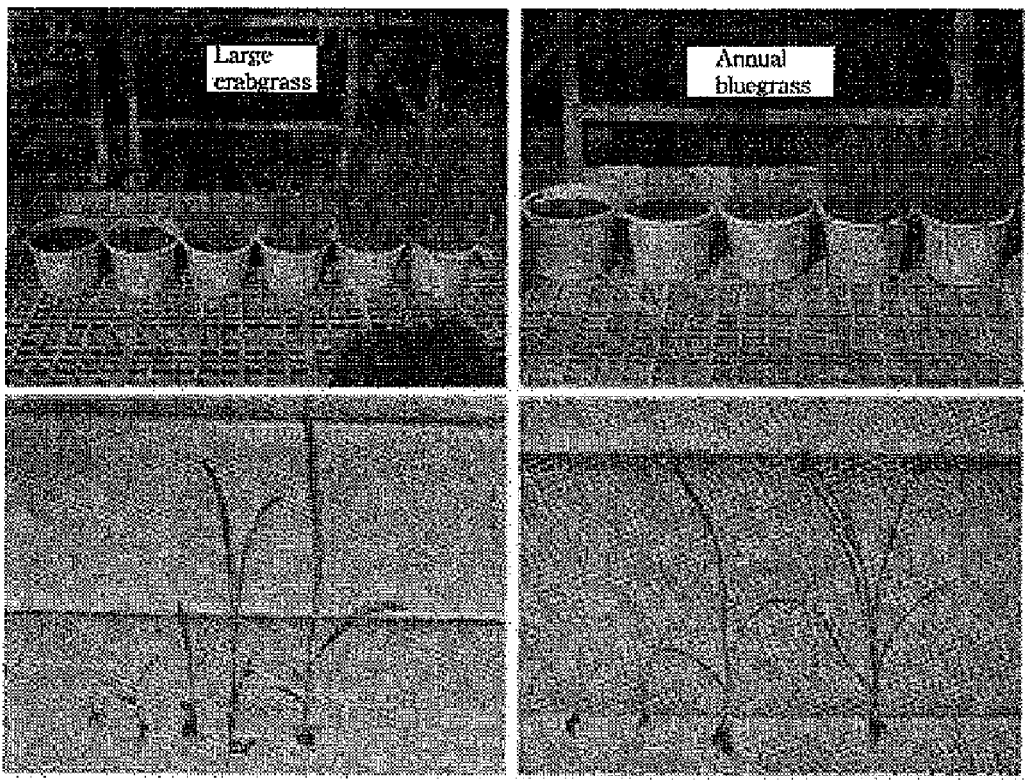
FIG. 6 shows large crabgrass and annual bluegrass at different growth stages. Large crabgrass and annual bluegrass used in the present invention include those at one-to five-leaf stages.
Figure 7:
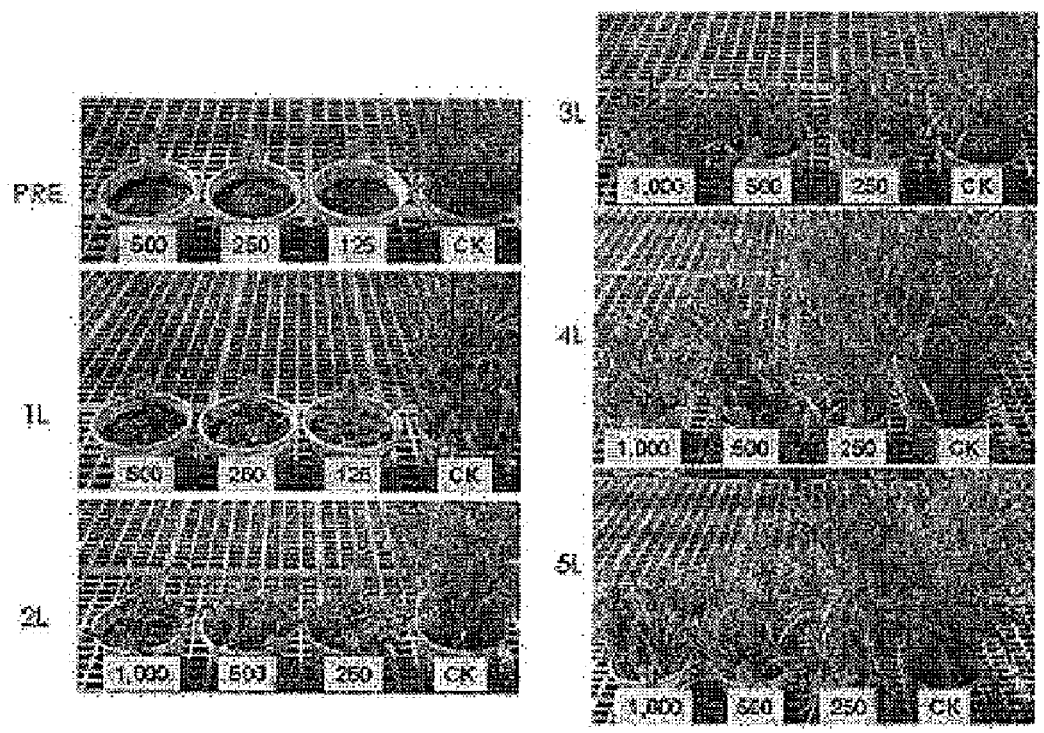
FIG. 7 shows the effect of the test substance of the present invention tested for large crabgrass. From the photo on the far left side, it represents pre-emergence (PRE) stage, and 1 leaf stage (1L) to 5-leaf stage (5 L). CK indicates untreated control.
Figure 8:
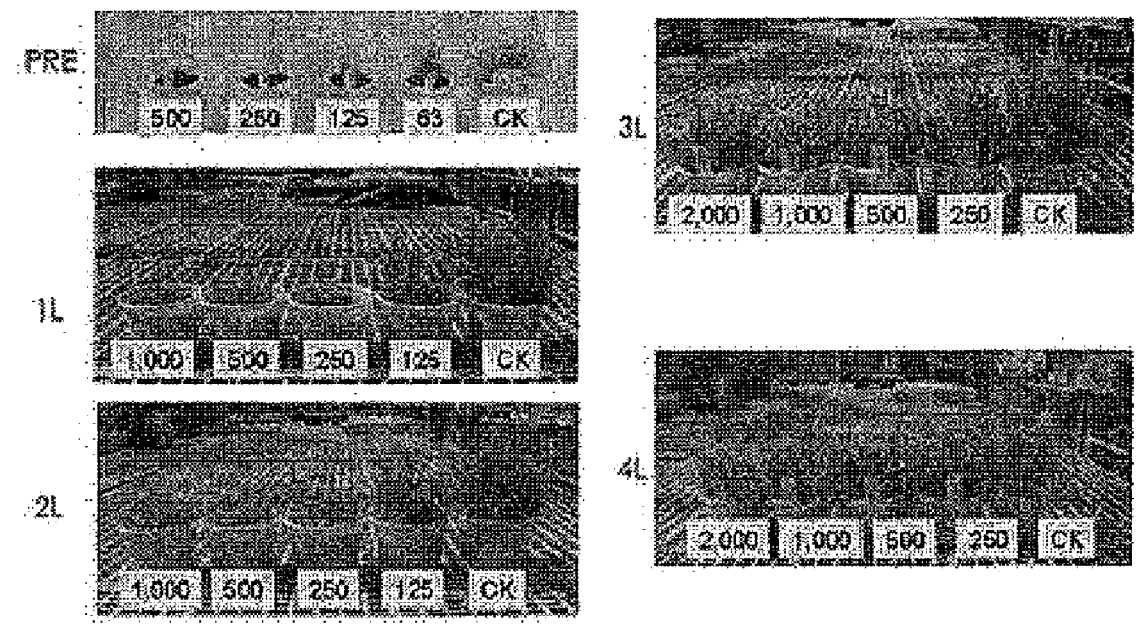
FIG. 8 shows the effect of the test substance of the present invention for annual bluegrass.

According to the above-described results of Table 2, it was found that the test substance of the present invention had an excellent safety to all types of the turfgrasses even at very high dosage of 4 kg/ha, and there was almost no phytotoxic effect when the dosage was the same or less than 0.5 kg/ha (see, FIG. 4 and FIG. 5). Compared to the reference herbicide Dithiopyr at the recommended rate (0.48 kg/ha), negligible phytotoxicity was observed with the test substance of the present invention even at 1~2 kg/ha. Thus, it is evident that the test substance of the present invention is far safer than Dithiopyr which has been widely used as a turf grass herbicide (see, FIG. 3). In addition, since the test substance of the present invention controls large crabgrass almost completely by pre-emergence application at a dosage as low as 0.06~0.12 kg/ha (see, the results of Table 1), it can be used in a wide dose range between 0.06 and 2 kg/ha for turf.

Example 3

Measurement of Herbicidal Activity for Large Crabgrass and Annual Bluegrass at Different Growth Stages The most common problematic gramineous weed in turf includes annual bluegrass in addition to large crabgrass. While large crabgrass is an annual grass which usually emerges during spring season, annual bluegrass is a biennial weed which germinates during fall season or sometimes during winter and spring season when temperature is cool.

According to the result of Table 1, although the efficacy is lower in post-emergence treatment compared to pre-emergence treatment, the test substance of the present invention showed an herbicidal activity to growing weeds at higher rates. Thus, in this experiment, efficacy was more carefully evaluated in different application timing for large crabgrass and annual grass.

To a cup pot having a surface area of 100 cm$^2$ wherein mixed soils comprising blend bed soil (Boonong, Horticultural Bed Soil No. 3) and sandy loam soil were filled (mixing ratio, 1:1), seeds of large crabgrass and annual bluegrass were sown consecutively at an one week interval. The pots were moistened by sub-irrigation, and kept in a greenhouse maintained at 25~30° C. (day) or 15~25° C. (night). The said weeds were grown to various growth stages from pre-emergence to the four-leaf stage. Then, they were applied with the test substance of the present invention at dosage of 2, 1, 0.5, or 0.25 kg/ha. As a reference herbicide, Dithiopyr (32% EC, manufactured by Dongbu Hannong Chemical Company), was applied at 0.96, 0.48, or 0.24 kg/ha. Spray volume was adjusted to 2,000 L/ha. The method to spray of the test substance and prepare spray solutions were the same as described above. The reference herbicide was used after it was diluted with 0.2% (v/v) Tween 20 aqueous solution. The test was conducted in a randomized block design with three replicates. Two weeks after the treatment, plant parts remained above the pot soil surface were cut and the fresh weight was weighed. Results are given by a suppression ratio relative to the biomass that was obtained from the untreated group (see, Table 3).

TABLE 3

Herbicidal effect of the test substance to large crabgrass and annual bluegrass at different growth stages*

| Herbicide | Dosage (kg/ha) | Large crabgrass | | | | | Annual bluegrass | | | | |
|---|---|---|---|---|---|---|---|---|---|---|---|
| | | PRE | 1 leaf | 2 leaf | 3 leaf | 4 leaf | PRE | 1 leaf | 2 leaf | 3 leaf | 4 leaf |
| Test substance | 2 | 100 | 100 | 98 | 97 | 76 | 100 | 99 | 95 | 69 | 60 |
| | 1 | 100 | 100 | 98 | 94 | 70 | 100 | 97 | 93 | 66 | 55 |
| | .5 | 100 | 100 | 93 | 86 | 65 | 100 | 96 | 90 | 61 | 37 |
| | .25 | 100 | 100 | 81 | 72 | 33 | 100 | 95 | 82 | 18 | 2 |
| | .12 | 84 | 95 | 45 | 23 | 16 | 95 | 37 | 35 | 0 | 0 |
| Dithiopyr | .96 | 100 | 100 | 98 | 89 | 66 | 100 | 97 | 91 | 61 | 35 |
| | .48 | 100 | 100 | 95 | 89 | 57 | 100 | 95 | 88 | 44 | 10 |
| | .24 | 100 | 100 | 89 | 86 | 56 | 100 | 90 | 87 | 46 | 4 |

*suppression ratio relative to the biomass obtained from the untreated group (%)

The test substance of the present invention suppressed both large crabgrass and annual bluegrass from PRE (pre-emergence) to 2-leaf stage by ≧90% at 0.5 kg/ha or above. Large crabgrass over four-leaf stage and annual bluegrass over three-leaf stage were suppressed but were not completely controlled. When the test substance was used at a dosage of ≧1 kg/ha or more for large crabgrass at 3-leaf stage, 90% or more were suppressed. Similar tendency was found for Dithiopyr.

Taken together, the results of Table 2 and Table 3, it is confirmed that the test substance of the present invention has high safety for cold and warm season turfgrass at a dosage as high as 4 kg/ha, while can effectively control major gramineous weeds such as large crabgrass and annual bluegrass during a period from pre-emergent (PRE) to two-leaf stage at a dosage of 0.5 kg/ha and above.

Example 4

Evaluation of Herbicidal Activity of the Test Substance in Direct-seeded Rice Plants The herbicidal use for rice paddy field disclosed in Korean Patent Registration No. 0392072 refers to an application of the herbicide on paddy water in which rice plants are been transplanted, which is a typical practice in Korea and Japan. In US, Europe and Southeast Asia regions, rice seeds are directly sown and herbicides are usually foliarly sprayed in the same way as used for upland crops; it is completely different from the transplanted rice practiced in Korea and Japan.

For such reason, in the present invention the test substance was tested for direct-seeded rice by foliar spray which is a different method from that disclosed in Korean Patent Registration No. 0392072. To a cup pot having a surface area of 100 cm$^2$ wherein mixed soils comprising blend bed soil (Boonong, Horticultural Bed Soil No. 3) and sandy loam soil were filled (mixing ratio, 1:1), seeds of rice (cv. MT101, an Indica type cultivar), and problematic gramineous rice weeds including barnyardgrass, Chinese sprangletop (*Leptochloa chinensis*), saramollagrass (*Ischaemum rugosum*), *Ishachne globosa* were sown. The pots were sub-irrigated and kept in a greenhouse maintained at 25~30° C. (day) or 15~25° C. (night). Fourteen days after the sowing, when the crop plant and said weeds reached around 3-leaf stage, sets of rice and weed pots were prepared again as described above, and then the test substance was sprayed over them. In this case, the spray treatment to the plants grown for two weeks corresponded to post-emergence treatment while the spray treatment to the seeds right after the sowing corresponded to pre-emergence treatment. Spray was made by a track sprayer equipped with a Teejet 8002 nozzle and the spray volume was adjusted to 300 L/ha. By dissolving the test substance in acetone and adding the same volume of 0.2% (v/v) Tween 20 aqueous solution, the spray solution was prepared. Dosage of the sprayed substance was 500, 250, 125, 62.5 or 31.3 g ai/ha. Two weeks after the spray of the test substance, efficacy and phytotoxic effect to the crops and the weeds were visually measured based on a 0 to 10 scale (0: no efficacy, 10: completely killed). The results are summarized in the following Table 4.

TABLE 4

Treatment results with the test substance to the direct-seeded rice and gramineous weeds

| Dosage (g/ha) | Rice (MT101) | Barnyard grass | Leptochloa chinensis | Ischaemum rugosum | Isachne globasa |
|---|---|---|---|---|---|
| Pre-emergence treatment; soil treatment | | | | | |
| 500 | 0 | 10 | 10 | 10 | 10 |
| 250 | 0 | 10 | 10 | 10 | 10 |
| 125 | 0 | 10 | 10 | 10 | 10 |
| 62.5 | 0 | 8 | 10 | 9 | 10 |
| 31.25 | 0 | 7 | 10 | 8 | 9 |
| Post-emergent treatment: foliar spray to 3-leaf stage rice and weeds | | | | | |
| 500 | 2 | 10 | 10 | 10 | 10 |
| 250 | 2 | 10 | 9 | 10 | 10 |
| 125 | 1 | 9 | 8 | 7 | 10 |
| 62.5 | 0 | 8 | 5 | 6 | 7 |
| 31.25 | 0 | 4 | 4 | 3 | 5 |

*visual measurement: 0, no phytotoxic effect/no efficacy; 10, completely killed

In the pre-emergence application, the test substance of the present invention showed an excellent controlling effect for all of the tested gramineous weeds at a dosage of 125 g/ha or more without having any phytotoxic effect to the rice plant. In addition, in the post-emergence application, the test substance of the present invention showed an excellent controlling effect for all of the tested gramineous weeds at a dosage of 250 g/ha or more with only minimal (acceptable) phytotoxic effect to the rice, indicating that it has an excellent applicability to direct-seeded rice.

Effect Of The Invention

As demonstrated by the above examples, the present invention confirms that the derivatives having general formula (I) as disclosed in Korean Patent Registration No. 392072 and 5-(2,6-difluorobenzyl)oxymethyl-5-methyl-3-(4-methylthiophen-5-yl)-1,2-isoxazoline compound, and the representative example compound as described by the formula (II), which had been disclosed as a useful paddy herbicide, have a high safety to upland crops, turfgrass, and direct-seeded rice and can control various grass weeds. As such, the said compounds can be used as an upland crop herbicide, a turf herbicide and a herbicide for a direct-seeded rice with high safety and an excellent herbicidal activity.

What is claimed is:

1. A method of selectively controlling large crabgrass in turf grass, which comprises the steps of:

obtaining 5-benzyloxymethyl-1,2-isoxazoline derivative compounds of the following formula (I) as an active ingredient:

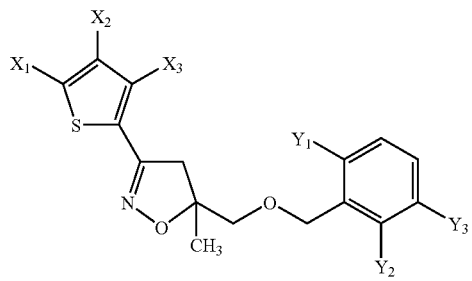

wherein, $X_1$, $X_2$ and $X_3$ are each a hydrogen, a methyl group, a halogen group, a methoxy group or a nitro group, provided that all of $X_1$, $X_2$ and $X_3$ cannot be a hydrogen at the same time; and $Y_1$, $Y_2$ and $Y_3$ are each a hydrogen or a fluorine; and applying said derivative compounds, pre-emergence or post-emergence to large crabgrass in turf grass.

2. The method according to claim 1, wherein the said 5-benzyloxymethyl-1,2-isoxazoline derivative compound is 5-(2,6-difluorobenzyfloxymethyl-5-methyl-3-(4-methylthiophen-5-yl)-1,2-isoxazoline compound that is represented by the following formula (II):

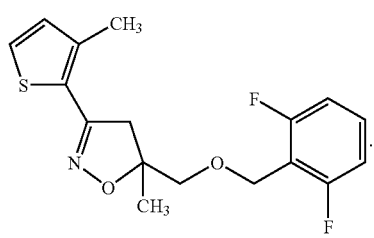

3. The method according to claim 1, wherein the compound of the formula (I) is comprised, as a single active ingredient, of 1 to 80% by weight in a final formulated product.

4. The method according to claim 1, wherein the compound of the formula (I) is comprised, as an active ingredient in a mixture with one or more other active ingredient(s), of 1 to 40% by weight in a final formulated product.

5. The method according to claim 1, wherein the turf grass comprises at least one of a warm season turf grass and a cool season turf grass, and the warm season turf grass is zoysiagrass, and the cool season turf grass is bentgrass, Kentucky bluegrass or perennial ryegrass.

6. The method according to claim 1, wherein the turf grass comprises a warm season turf grass.

7. The method according to claim 1, wherein the turf grass comprises a cool season turf grass.

8. The method according to claim 7, wherein the cool season turf grass is bentgrass.

9. The method according to claim 7, wherein the cool season turf grass is Kentucky bluegrass.

10. The method according to claim 7, wherein the cool season turf grass is perennial ryegrass.

* * * * *